United States Patent [19]

Su et al.

[11] Patent Number: 5,279,946

[45] Date of Patent: Jan. 18, 1994

[54] PROCESS FOR THE PREPARATION OF N-BENZYLOXYCARBONYL-ALPHA-L-ASPARTYL-L-PHENYLALANINE METHYL ESTER

[75] Inventors: Chein-Shyong Su; Huey-Lin Chung; Wuen-Hsian Huang; Hsin Tsai, all of Taipei, Taiwan

[73] Assignee: Development Center for Biotechnology, Taipei, Taiwan

[21] Appl. No.: 727,696

[22] Filed: Jul. 10, 1991

[51] Int. Cl.$^5$ .............................................. C12P 21/02
[52] U.S. Cl. ................................. 435/68.1; 435/108; 435/109; 435/129
[58] Field of Search ...................... 435/68.1, 108, 109, 435/129

[56] References Cited

U.S. PATENT DOCUMENTS 4,116,768  9/1978  Isowa et al. ..................... 435/68.1
4,935,355  6/1990  Ulmer et al. ..................... 435/68.1

OTHER PUBLICATIONS

Nakanishi et al., "Continuous Synthesis of N–(Benzylcrycarbonyl)-L-Aspartyl-L-Phenylalanine Methyl Ester with Immobilized Thermolysin in an Organic Solvent," *Biotechnology*, vol. 3, pp. 459–464, 1985.

Nakanishi et al., "Kinetics and Equilibruim of Enzymatic Synthesis of Peptides in Aqueous Organic Biphanic Systems," *Eur. J. Biochem.* vol. 161, pp. 541–549 (1986).

Nakamura et al, "N . . . Production by Immobilized *Nocardia opaca*: Thermolysin under Hydrogen High Pressure in a Water Organic Solvent System," *J. Ferment. Bioenginer* vol. 67, No. 6 pp. 399–403 1989.

Toi et al., "Papain Catalyzed Esterfication in Polar, Organic Solvents," *Biotech Letters*, vol. 11, No. 3 pp. 173–176 1989.

*Primary Examiner*—Marian Knode
*Attorney, Agent, or Firm*—Townsend and Townsend

[57] ABSTRACT

Disclosed is a process for the preparation of N-benzyloxycarbonyl-α-L-aspartyl-L-phenylalanine methyl ester wherein a protease is used to catalyze the condensation reaction of N-benzyloxycarbonyl-L-aspartic acid with L-phenylalanine methyl ester in a system consisting of ethyl acetate, citrate buffer with the addition of glycerol as a dispersing agent.

7 Claims, No Drawings

PROCESS FOR THE PREPARATION OF N-BENZYLOXYCARBONYL-ALPHA-L-ASPARTYL-L-PHENYLALANINE METHYL ESTER

FIELD OF THE INVENTION

The present invention relates to a process for efficiently condensing N-benzyloxycarbonyl-L-aspartic acid and L-phenylalanine methyl ester to form N-benzyloxycarbonyl-α-L-aspartyl-L-phenylalanine methyl ester using a proteolytic enzyme having a broad range of peptidase and esterase activity.

BACKGROUND OF THE INVENTION

Whittaker (WO 8706268, 1987) discovered that papain could efficiently catalyze the reaction of N-benzyloxycarbonyl-L-aspartic acid dibenzyl ester with L-phenylalanine methyl ester to form N-benzyloxycarbonyl-α-L-aspartyl (β-benzyl ester )-L-phenylalanine methyl ester, an aspartame precursor. A disadvantage of this process is that the N-benzyloxycarbonyl-L-aspartic acid dibenzyl ester, which is used as the enzyme substrate, has to be prepared from N-benzyloxycarbonyl-L-aspartic acid and benzyl alcohol. Therefore, this process is complicated.

Condensation reaction of N-benzyloxycarbonyl-L-aspartic acid with L-phenylalanine methyl ester to form N-benzyloxycarbonyl-α-L-aspartyl-L-phenylalanine methyl ester, an aspartame precursor, has been described by Chen and Wang (*J. Org. Chem.* 52, 4589-4590, 1988). However, a lower yield (70 %) is obtained and more enzyme and longer reaction time (72 hours) are required in accordance with this process.

Furthermore, in the process of preparing N-benzyloxycarbonyl-α-L-aspartyl-L-phenylalanine methyl ester by papain, the product will be accumulated in the form of a cake and be easily hydrolyzed further by papain to give N-benzyloxycarbonyl-α-L-aspartyl-L-phenylalanine which is an undesirable by-product.

SUMMARY OF THE INVENTION

It is therefore an object of the present invention to provide a process for the preparation of N-benzyloxycarbonyl-α-L-aspartyl-L-phenylalanine methyl ester, by which the reaction time can be shortened, the yield can be improved and also cake formation can be prevented and the resulting product can be recovered from the reaction mixture in a partially purified form by simple extraction method.

To achieve the above object, during the course of investigation of the use of papain in enzymatic peptide synthesis, the inventors found that papain is capable of efficiently catalyzing the reaction of N-benzyloxycarbonyl-L-aspartic acid with L-phenylalanine methyl ester in a two phase system containing ethyl acetate and potassium citrate buffer with the addition of glycerol as a dispersing agent. The reaction leads to high yield of N-benzyloxycarbonyl-α-L-aspartyl-L-phenylalanine methyl ester which can be recovered in a partially purified form by simple extraction method. The critical event that led to the success of the process of the present invention was the overcoming of a serious difficulty encountered in a conventional process due to the formation of a viscous aggregate in the reaction mixture.

In accordance with the present invention, the process for the preparation of N-benzyloxycarbonyl-α-L-aspartyl-L-phenylalanine methyl ester comprises condensing N-benzyloxycarbonyl-L-aspartic acid with L-phenylalanine methyl ester in the presence of proteolytic enzyme in aqueous buffer-ethyl acetate two phase system with the addition of glycerol as a dispersing agent at a pH ranging from 3.0 to 7.5 and a temperature ranging from 25° to 49° C.

According to one aspect of the present invention, the proteolytic enzyme is papain and the aqueous buffer is sodium citrate buffer or potassium citrate buffer.

According to another aspect of the present invention, the product of the process can be recovered from the reaction mixture and partially purified by simple extraction process using potassium phosphate buffer and hydrochloric acid consecutively.

DETAILED DESCRIPTION OF THE INVENTION

The advantages, features and process of the present invention will be described in detail by reference to the following examples.

EXAMPLE 1

Papain (1 g; obtained from J. E. Siebel Son's Co.) was well suspended in 2 ml of 3.0M potassium citrate buffer (pH 5.1), the suspension was then mixed with 2 ml of glycerol. To 100 ml of ethyl acetate, 80 mmole of L-phenylalanine methyl ester hydrochloride and 80 mmole of triethylamine were added and stirred at 25° C. for 40 min then 40 mmole of N-benzyloxycarbonyl-L-aspartic acid was added and stirred for 20 min. The whole ethyl acetate mixture, containing soluble L-phenylalanine methyl ester and N-benzyloxycarbonyl-L-aspartic acid and insoluble triethylamine hydrochloride, w-as subsequently added to the papain suspension. The reaction mixture was stirred at 25° C. for 22 hr then 200 ml of ethyl acetate was added and stirred at 55° C. for 15 min and filtered. As determined by HPLC analysis the yield of the N-benzyloxycarbonyl-α-L-aspartyl-L-phenylalanine methyl ester in the filtrate was 85% calculated on the basis of the initial amount of the N-benzyloxycarbonyl-L-aspartic acid. The ethyl acetate solution was then extracted twice with 150 ml of 0.01M phosphate buffer (pH 7.0), then twice with 150 ml of 0.3N hydrochloric acid. The final organic layer was dehydrated with 10 g of anhydrous $Na_2SO_4$, then evaporated and vacuum dried to give 17.4 partially purified N-benzyloxycarbonyl-α-L-aspartyl-L-phenylalanine methyl ester.

EXAMPLE 2

The process of Example 1 was repeated, except that the molar ratio of N-benzyloxycarbonyl-L-aspartic acid to L-phenylalanine methyl ester hydrochloride to triethylamine was 4:6:6 and the reaction time for condensation was 48 hr. The yield of N-benzyloxycarbonyl-α-L-aspartyl-L-phenylalanine methyl ester was 80%.

EXAMPLE 3

Papain (1 g, obtained from Merck Co.) was well suspended in 2 ml of 3.0M potassium citrate buffer (pH 5.1), the suspension was then mixed with 2 ml of glycerol. To 100 ml of ethyl acetate 50 mmole of L-phenylalanine methyl ester hydrochloride and 50 mmole of trimethylamine were added and stirred at 25° C. for 40 min then 20 mmole of N-benzyloxycarbonyl-L-aspartic acid was added and stirred for 20 min. The whole ethyl acetate mixture, containing soluble L-phenylalanine methyl ester and N-benzyloxycarbonyl- L-aspartic acid and insoluble triethylamine hydrochloride, was subsequently added to the papain suspension. The reaction mixture was stirred at 25° C. for 28 hr. The yield of N-benzyloxycarbonyl-α-L-aspartyl-L-phenylalanine methyl ester was 73%.

EXAMPLE 4

The process of Example 3 was repeated, except that 15 g of papain, 4 ml of potassium citrate buffer (pH 5.1) and 12 ml of glycerol were used, and the reaction time for condensation was carried out at 49° C. for 5 hr. The yield of N-benzyloxycarbonyl-α-L-aspartyl-L-phenylalanine methyl ester was 81%.

EXAMPLE 5

The process of Example 3 was repeated, except that the pH of potassium citrate was 3.0, and the condensation reaction was carried out at 25° C. for 23 hr. The yield of N-benzyloxycarbonyl-α-L-aspartyl-L-phenylalanine methyl ester was 74%.

EXAMPLE 6

The process of Example 1 was repeated, except that the pH value of the buffer was 3.0, and 3.0M of sodium citrate buffer was used. The yield of N-benzyloxycarbonyl-α-L-aspartyl-L-phenylalanine methyl ester was 81%.

EXAMPLE 7

The process of Example 1 was repeated, except that the 3.0M sodium citrate buffer (pH 7.5) was used. The yield of N-benzyloxycarbonyl-α-L-aspartyl-L-phenylalanine methyl ester was 80%.

EXAMPLE 8

The process of Example 1 was repeated without addition of glycerol. The yield of N-benzyloxycarbonyl-α-L-aspartyl-L-phenylalanine methyl ester was 19.2%.

EXAMPLE 9

The process of Example 8 was repeated with the addition of 2 ml PPG-1025 (polypropylene glycol) as a dispersing agent, and the yield of N-benzyloxycarbonyl-α-L-aspartyl-L-phenylalanine methyl ester was 11.8%.

EXAMPLE 10

The process of Example 8 was repeated with the addition of 2 ml SPAN-80 as a dispersing agent, and the yield of N-benzyloxycarbonyl-α-L-aspartyl-L-phenylalanine methyl ester was 5.6%.

EXAMPLE 11

The process of Example 1 was repeated except using 1 ml of glycerol. The yield of N-benzyloxycarbonyl-α-L-aspartyl-L-phenylalanine methyl ester was 80.4%.

It is known from the above examples that according to the process of the present invention high yield of N-benzyloxycarbonyl-α-L-aspartyl-L-phenylalanine methyl ester is obtainable within a short reaction time. It is also known from Examples 8, 9 and 10 that the dispersing agent should be glycerol, and the yield will be reduced if other kinds of dispersing agents are used.

What is claimed is:

1. A process for the preparation of N-benzyloxycarbonyl-α-L-aspartyl-L-phenylalanine methyl ester comprising:
   a) combining papain in citrate buffer with glycerol said citrate buffer having a pH between 3.0 and 7.5;
   b) adding the citrate buffer of step (a) to a solution of N-benzyloxycarbonyl-L-aspartic acid an L-phenylalanine methyl ester in ethyl acetate;
   c) condensing the N-benzyloxycarbonyl-L-aspartic acid with the L-phenylalanine methyl ester through the action of the papain at a temperature of between 25° C. and 49° C to yield N-benzyloxycarbonyl-α-L-aspartyl-L-phenylalanine methyl ester; and
   d) recovering the N-benzyloxycarbonyl-α-L-aspartyl-L-phenylalanine methyl ester.

2. A process as claimed in claim 1, wherein said citrate buffer is sodium citrate buffer.

3. A process as claimed in claim 1, wherein said citrate buffer is potassium citrate buffer.

4. A process as claimed in claim 2, wherein the pH of said sodium citrate buffer is from 3 to 7.5.

5. A process as claimed in claim 3, wherein the pH of said potassium citrate is from 3 to 6.

6. A process as claimed in claim 1, further comprising the recovery of said N-benzyloxycarbonyl-α-L-aspartyl-L-phenylalanine methyl ester by extraction using potassium phosphate buffer and hydrochloric acid, consecutively, as solvents.

7. A process as claimed in claim 6, wherein the pH of said potassium phosphate is from 6 to 7 and the concentration is 50 mM.

* * * * *